United States Patent [19]

Lee

[11] 3,946,489
[45] Mar. 30, 1976

[54] DENTAL CLUTCH

[76] Inventor: Robert L. Lee, 22937 Grand Terrace Road, Colton, Calif. 92324

[22] Filed: Dec. 30, 1974

[21] Appl. No.: 537,576

[52] U.S. Cl. .................................................. 32/17
[51] Int. Cl.² ............................................ A61C 9/00
[58] Field of Search ........................... 32/17, 18, 19

[56] References Cited
UNITED STATES PATENTS

| | | | |
|---|---|---|---|
| 2,963,786 | 12/1960 | Browning | 32/17 |
| 3,360,860 | 1/1968 | Roland | 32/17 |
| 3,464,115 | 9/1969 | Baker | 32/19 |
| 3,724,099 | 4/1973 | Stuart | 32/19 |
| 3,813,780 | 6/1974 | Dragan | 32/19 |

Primary Examiner—Louis G. Mancene
Assistant Examiner—J. Q. Lever
Attorney, Agent, or Firm—Knobbe, Martens, Olson, Hubbard & Bear

[57] ABSTRACT

A dental clutch member molded in the form of a thin-walled shell fits over the person's lower teeth and is attached thereto by plaster. Holes in the walls of the shell help the plaster become firmly attached to the shell. Support structure molded integral with the shell extends outwardly through the patient's mouth for receiving a horizontal rod to which is attached other dental apparatus. Fracture lines in the shell and the extension permit the shell to be broken into pieces to facilitate removal of the clutch from the patient. One or more tooth separators are molded with the clutch member and then broken away from the shell to be releasably attached to the clutch by detent buttons.

22 Claims, 7 Drawing Figures

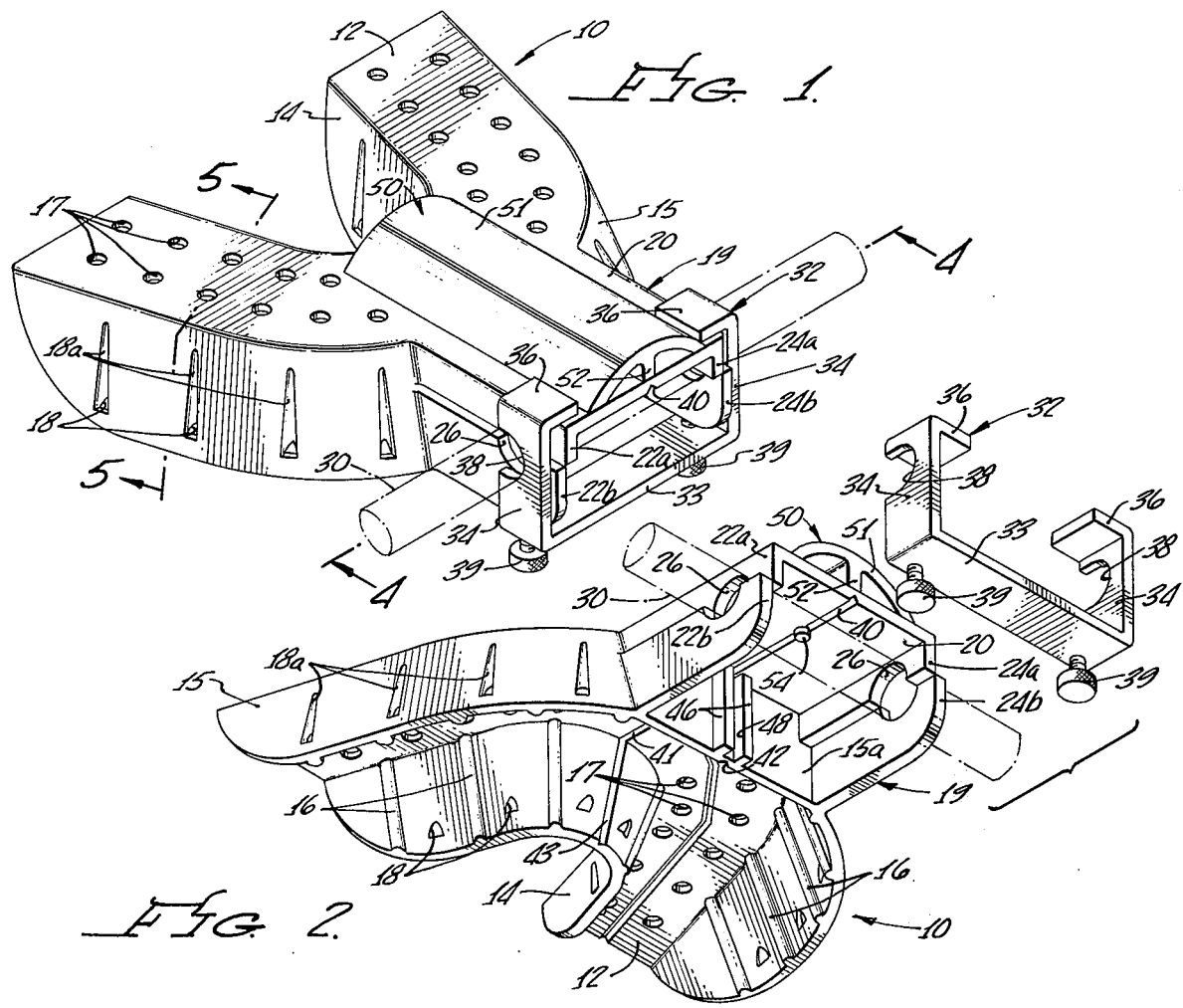
FIG. 1.
FIG. 2.
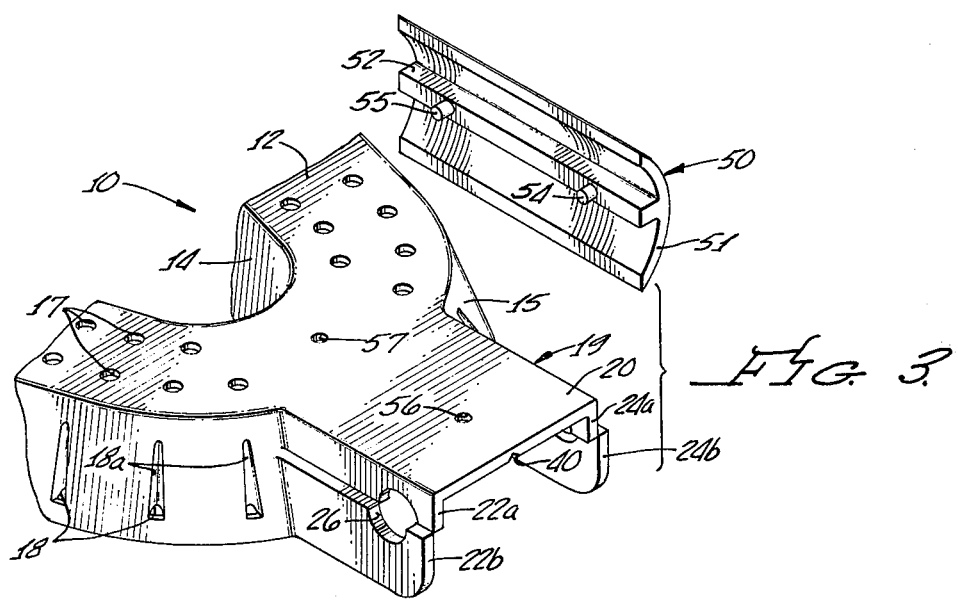
FIG. 3.

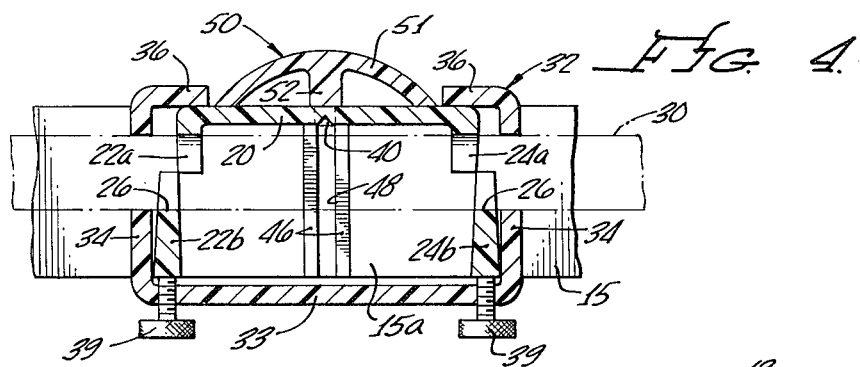
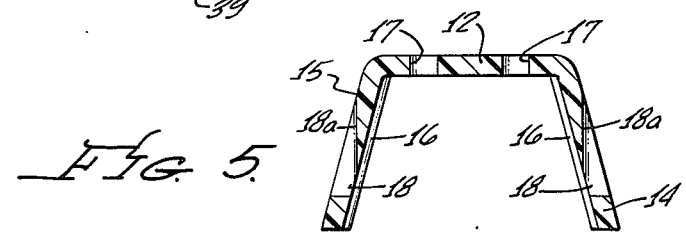
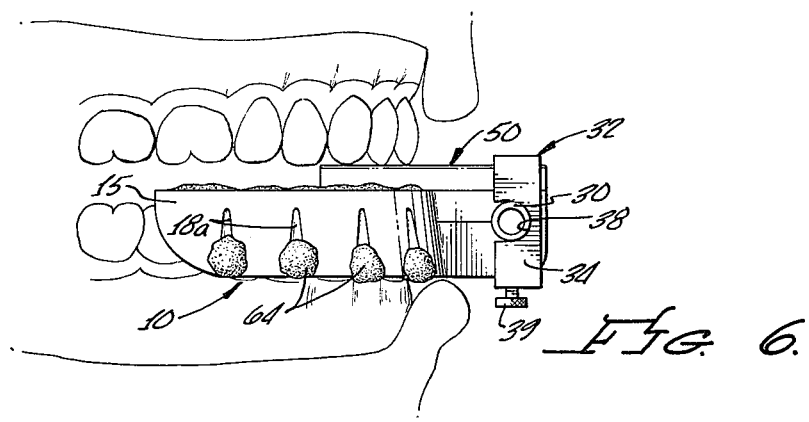
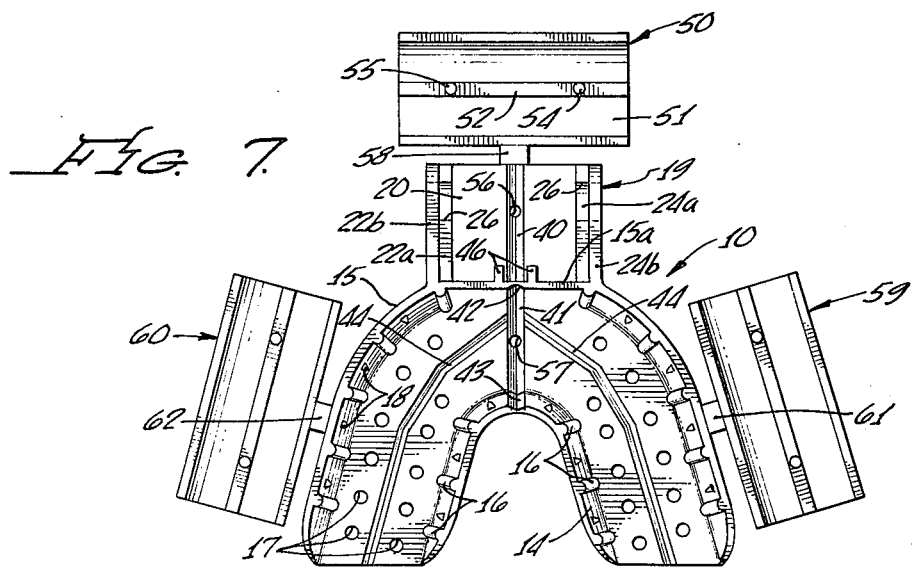

DENTAL CLUTCH

This invention relates to dental apparatus and more particularly to an improved clutch to be attached to the patient's teeth to support other diagnostic dental apparatus.

In making jaw measurements or performing other diagnostic dental analysis, it is often necessary to mount equipment to the patient's jaw. One known way to accomplish this is to mount the equipment to a clutch which fits over the teeth of one jaw and is attached to the teeth by plaster or other temporary bonding material. The clutch itself is often made of smooth imperforate metal for durability and sanitation. A thermosetting compound is positioned in the clutch and the clutch is placed over the teeth. The compound attaches to the clutch and makes a mold of the teeth, however, it does not adhere to the teeth because of moisture on the teeth. A coating of zinc oxide eugenol paste is therefore applied to the thermosetting mold which will bond the mold to the teeth. Removal of the clutch is somewhat difficult and time consuming. Also, the thermosetting material attached to the clutch must then be removed from the clutch, and the clutch resterilized for use on another patient.

Another disadvantage of the present arrangement is that the cost of the clutch is such that it is often not practical to have a variety of sizes. Consequently some clutches are made adjustable, which lends versatility but further adds to the cost. Even with adjustability however there are some situations in which the clutch does not fit properly on the patient's teeth, which can add further difficulties for the patient and the dentist.

While performing jaw measurements, it is often desirable to separate the patient's upper and lower teeth sufficiently so that they do not interfere with the jaw movements. For this purpose a tooth separator is sometimes employed. Various separators are utilized all having some advantages and disadvantages. The need still exists for further improvements in that area both with respect to cost and function.

The present invention overcomes some of the prior art shortcomings. In accordance with the invention, a clutch is provided which can be attached to the patient's teeth by plaster which is easy to work with, and much less expensive than the attaching materials being currently used. In order to facilitate the use of plaster, the clutch of the invention is provided with a plurality of small holes so that when the clutch containing wet plaster is placed onto the patient's teeth, some of the plaster will ooze through the openings to help secure the clutch to the material as it hardens.

As a further important feature of the invention, the clutch is made of a moldable readily breakable material such as plastic acrylic. By forming fracture lines on the interior wall of the clutch, the clutch may be readily broken into two or more pieces with a simple tool such as a screwdriver. The plaster will often break with the clutch because of the small lugs of plaster extending through the holes in the clutch. Consequently, the broken sections of the clutch and plaster will readily fall away from the patient's teeth. The cost of such a plastic clutch is such that it is practical to discard the broken sections after use which further eliminates the cost of cleaning and sterilizing the clutch for future use, as is necessary with the prior art reusable clutches. The cost of the clutch can be further minimized by forming it with relatively thin walls having a plurality of reinforcing ribs, preferably extending vertically along the side walls of the clutch.

As a further feature, the clutch is formed with an extension structure on its forward portion to which may be attached a horizontal rod for mounting the dental diagnostic equipment to be utilized. The structure includes a horizontal wall which is an extension of the horizontal wall of the clutch, together with two side walls formed integral with the outer side wall of the main clutch portion. The side walls have holes formed therein for receiving the rod, with the holes preferably being formed of two laterally offset sections which facilitate the molding operation and also enable the plastic side walls to grip the rod. If further gripping force is required, there is also provided a clamp which fits over the clutch extension to apply force to the structure engaging the rod.

In addition to forming a means for mounting the rod, the extension serves as a base for receiving a tooth separator mounted on the upper surface of the extension. In a preferred approach, the tooth separator is also made of plastic material and is provided with a pair of buttons which snap into two holes on the clutch extension. The purpose for making the separator removable is that in some instances no separator is desired and separators of various sizes may be easily attached to the clutch. Tooth separators of various sizes may be molded simultaneously with the clutch and attached to the clutch by breakaway sections of plastic so that the entire unit may be supplied to the dentist in a sealed sterilized package. Thus the dentist may simply break open the package and select the tooth separator desired and either discard or save the other size separators for future use.

Further features and advantages of the invention will become apparent with reference to the following drawings in which:

FIG. 1 is a top perspective view of the clutch of the invention with a horizontal rod being shown in phantom lines supported by the clutch;

FIG. 2 is a bottom perspective view of the assembly of FIG. 1 showing the clamp separated from the clutch;

FIG. 3 is a top perspective view of the clutch showing the tooth separator removed from the clutch and showing the means for attaching the separator to the clutch;

FIG. 4 is an enlarged front elevational view of a portion of the clutch assembly illustrating the laterally offset side wall sections of the clutch or extension;

FIG. 5 is a cross sectional view through one side section of the clutch illustrating the configuration of the side walls and the holes through the side walls and the horizontal wall;

FIG. 6 is a schematic illustration of the clutch assembly in use on a patient's jaw; and FIG. 7 is a bottom plan view of the clutch with three tooth separators attached to the clutch by breakaway plastic sections.

Referring first to FIGS. 1 and 2, it may be seen that the clutch includes a main shell section 10 having an overall generally U-shaped configuration and further having an inverted U-shaped cross section, as may be seen from FIG. 5. The shell 10 has an upper horizontal wall 12 and inner and outer depending side walls 14 and 15 which flare outwardly somewhat.

The clutch is preferably made of a non-toxic, moldable material which is relatively strong and rigid but yet is somewhat flexible and further is somewhat brittle so that it is easily breakable if the wall is sufficiently thin.

Further, the material should be easily machineable or be capable of being ground away in the event it requires any adjustments for use on a patient. To reduce the size or the mass of the clutch, the walls are made relatively thin; however, to increase their strength the clutch is provided wiith a plurality of generally vertically extending ribs 16, as is best seen in FIG. 2. The material should also be relatively inexpensive so that the clutch can be economically disposable after one use. A material having the necessary characteristiics enumerated is acrylic plastic. Other suitable materials may also be available.

To facilitate attachment of the clutch to a patient's teeth, the upper horizontal wall 12 of the shell 10 is formed with two rows of holes 17 while both the inner and outer side walls 14 and 15 are formed with openings 18 which have been formed in the mold by vertically extending pins which create elongated recesses 18a in the outer surface of the outer wall 15, as may be seen in FIG. 5.

The clutch further includes a forwardly extending structure 19 for supporting dental apparatus to be used with the clutch. Such structure includes an upper wall 20 which is an extension of the horizontal wall 12 of the main shell, and a pair of side walls 22 and 24 which extend downwardly from the horizontal wall 20 and are formed integral with the forward central portion 15a of the outer wall 15 of the main shell. As seen from FIGS. 1 and 2, the side wall 22 has an upper section 22a outwardly offset the thickness of the wall from a lower section 22b. The wall 24 has similar sections 24a and 24b. A hole 26 is formed in each of the side walls through the adjoining edge of the upper and lower sections of the side walls so that one half of the hole is defined by the lower section the other half of the hole is defined by the upper section. Having the lower section offset from the upper section facilitates the molding operation. Also, since the sections are actually separate along their common edge, the offset arrangement further facilitates the gripping of a horizontal rod 30, shown in phantom lines in FIG. 1. The holes 26 in the side walls 22 and 24 are aligned so that the rod 30 is supported in generally horizontal position perpendicular to the side walls and parallel to the upper horizontal wall 20. The diameter of the hole 26 is slightly smaller than the diameter of the rod 30 so that the slight flexibility of the upper and lower side wall sections tend to cause them to grip the rod and hold it stable. Preferably the rod is knurled around its midsection to further prevent rotation of the rod.

As another means for providing additional gripping of the rod, there is provided a box-like clamp 32 which fits over the clutch support structure 19. More specifically the clamp includes a bottom horizontal wall 33, a pair of upwardly extending side walls 34 and a pair of inwardly extending short stub walls 36. The side walls are formed with semicircular recesses 38 which receive the rod 30 and enable the clamp to be slipped over the end of the support structure 19. A pair of screws 39 are threadably mounted in the bottom horizontal wall 33 on lines intersecting the rod 30. These screws when tightened engage the lower edge of the side wall lower sections 22b and 24b of the extension structure 19 causing the upper stub walls to press downwardly on the horizontal wall 20, thus urging the upper wall sections 22a and 24a downwardly. This action increases the gripping force on the rod 30.

To facilitate removal of the clutch from a patient's teeth, the lower surface of the horizontal extension wall 20 is formed with a fracture line 40, as may be seen from FIGS. 2 and 7. This line has a V-shaped cross section such that the bottom of the V is relatively thin so that the material can be readily broken along this line. As further seen from FIGS. 2 and 7, the lower surface of the upper horizontal wall 12 of the shell also has a fracture line 41 aligned with the line 40. The forward central section 15a of the outer side wall 15 of the clutch shell 10 is formed with a fracture line 42 on its inner surface which intersects the fracture lines 40 and 41. The forward surface of the inner side wall 14 is likewise formed with a fracture line 43 in the same plane with the other lines. Thus the series of fracture lines 40-43 together bisect the clutch into left and right sections. An additional fracture line 44 is formed along the lower surface of the upper horizontal wall 12 between the rows of holes 17, thus further dividing the clutch into rear portions and forward portions.

Referring to FIG. 2, it may be seen that the outer surface of the vertical forward section 15a of the outer wall 15 of the shell 10 is formed with two outwardly extending ribs 46 on each side of the vertical fracture line 42. These ribs define a slot 48.

Also shown in FIGS. 1-4 is a tooth separator 50 having a smooth upper curved or arcuate section 51 and a centrally located depending wall or rib 52. Formed integral with and depending from the rib 52 are a pair of spaced buttons 54 and 55. These buttons are adapted to be received within a pair of spaced apertures 56 and 57, the forward aperture 56 being located in the horizontal wall 20 of the forward support structure 19 and being adapted to receive the forward button 54. The rear aperture 57 is formed in the horizontal wall 12 of the main shell between the two rows of holes 17, and is adapted to receive the rear button 55 of the tooth separator.

The tooth separator 50 is molded of the same material as the clutch. It is desirable to have different sized tooth separators. Thus for example three different sizes may be conveniently molded with the clutch. Such an arrangement is shown in FIG. 7 wherein the clutch 50 is shown attached to the clutch by a breakaway section 58 and two additional tooth separators 59 and 60 are likewise shown attached to the clutch by breakaway sections 61 and 62. The tooth separators differ by virtue of having the central rib 52 being of different height so that the teeth of an upper and lower jaw may be further separated. Since it is desirable that the width of the tooth separator remain the same for each of the separators so as to be supported stably on the clutch, the curvature of the upper wall 51 varies as the height of the rib 52 varies.

In operation, a clutch together with one or more tooth separators as shown in FIG. 7 is provided in a sterilized package for convenience of use by dentists. The dentist simply selects the size clutch he thinks will fit, opens the package, breaks away the tooth separators 50, 59 and 60 and positions the clutch over the patient's teeth for size. If the clutch does not fit properly, portions can be easily ground away or can be softened by heat and then shaped as desired.

Once the fit is satisfactory, the rod 30 to which other dental apparatus is to be attached is inserted in the holes 26 of the side walls 22 and 24 of the forward extension structure 19. As has been explained, the offset upper and lower wall sections of the side walls 22 and 24 tend to grip the rod to hold it firmly in a selected position. Further if additional gripping is desired, the clamp 32 may be positioned on the extension, as described above.

To attach the clutch to the patient's teeth, a quantity of soft plaster is positioned within the main shell 10 and the shell positioned over the patient's teeth such as the teeth of the lower jaw as shown in FIG. 6. Since the plaster is soft, some of it will immediately ooze through the holes in the upper horizontal wall 12 of the shell and through the openings in the inner and outer side walls 14 and 15 of the shell. As the plaster hardens, the portions 64 which have oozed through these openings form a series of lugs which firmly attach the plaster to the clutch. The plaster, of course, enters the crevices and spaces between the teeth so that the clutch is thereby firmly easily attached to the teeth.

One of the many advantages of this arrangement is that the plaster is inexpensive and easy to use. Also it quickly hardens so that there is less delay and hence discomfort for the patient, as well as improving the dentist's efficiency.

Once the plaster has hardened, the dentist may snap the selected tooth separator 50 into position by inserting its buttons 54 and 55 into the mating apertures 56 and 57 in the clutch, as shown in FIGS. 2 and 3. As seen from FIG. 6, the patient's upper teeth engage the smooth upper curved wall 51 of the tooth separator 50 so that the upper teeth slide smoothly on the separator while the lower jaw is moved and yet the upper and lower teeth are suitably spaced so that the teeth do not interfere with the jaw movement.

When the dentist has completed his work it is a simple matter to remove the clutch from the patient's jaw. The flat tip of a tool, such as a screwdriver, is inserted within the slot 48 between the two vertically extending ribs 46 in the central section 15a of the outer wall 15, as seen in FIG. 2. By twisting the tip of the tool, a separating force is applied to the ribs 46 causing the clutch to break into left and right sections along the fracture lines 40–43. Also by this same action, the clutch will frequently break along the line 44 thus breaking the clutch into two more sections. If the clutch does not break on the line 44 with the action of the tool in the slot 48, the clutch may be broken along the fracture line 44 simply by prying upwardly under the lower forward edge of the outer wall 15 or the dentist may simply break the clutch along the line 44 with his fingers. Breaking the clutch in this manner typically causes the plaster to break iin the same manner. However, if all of the plaster does not break away with the clutch sections, it is very easy to remove the remaining plaster pieces in that the plaster does not have great adhesive qualities. The broken sections of the clutch along with the broken pieces of plaster can, of course, be simply discarded. Since both the clutch material and the plaster are relatively inexpensive, this is a practical procedure. Moreover it eliminates the expense of the time and material necessary to clean and sterilize a reusable clutch. Since sterilization procedures often leave much to be desired, a disposable clutch is also more sanitary for the patient.

What is claimed is:

1. A dental clutch comprising a member shaped to fit over the teeth of a human jaw including a horizontal wall to extend adjacent the crowns of the teeth and inner and outer side walls to fit over the sides of the teeth, said member being sized to permit a quantity of bonding material to fit around the teeth for securing the member to the teeth, said member having a plurality of small openings in one or more of its walls to permit some of said bonding material while in soft form to ooze through the openings so that when the material is hardened said member is securely attached to the teeth; and means in said member which permit it to be readily broken into two or more sections so as to facilitate removal of the clutch from the teeth.

2. The clutch of claim 1 wherein the member is made of breakable material which is also somewhat flexible, such as a plastic acrylic material, said member having fracture lines which bisect the member through the portion of the clutch member which fits over the front teeth to permit the member to be readily broken into sections.

3. The clutch of claim 2 wherein said member has a curved fracture line formed along the length of said horizontal wall that intersects the first mentioned fracture lines.

4. The clutch of claim 2 including means defining a slot in the front central part of said outer side wall on said fracture line, said slot being adapted to receive a tool, such as the tip of a screwdriver to facilitate breaking the clutch member into two pieces by twisting the tip of the screwdriver to apply pressure to both sections of the clutch.

5. A dental clutch comprising a member shaped to fit over the teeth of a human jaw including a horizontal wall to extend adjacent the crowns of the teeth and inner and outer side walls to fit over the sides of the teeth, said member being sized to permit a quantity of bonding material to fit around the teeth for securing the member to the teeth, said member having a plurality of small openings in one or more of its walls to permit some of said bonding material while in soft form to ooze through the openings so that when the material is hardened said member is securely attached to the teeth; and support means formed integral with the forward portion of the outer side wall for removably connecting the clutch member to a rod which extends generally horizontally to permit the attachment of other dental apparatus such as means for making jaw measurements, said means for attaching a clutch member to the rod including means defining a pair of spaced apertures which receive the rod with an interference fit.

6. A dental clutch comprising a member shaped to fit over the teeth of a human jaw including a horizontal wall to extend adjacent the crowns of the teeth and inner and outer side walls to fit over the sides of the teeth, said member being sized to permit a quantity of bonding material to fit around the teeth for securing the member to the teeth, said member having a plurality of small openings in one or more of its walls to permit some of said bonding material while in soft form to ooze through the openings so that when the material is hardened said member is securely attached to the teeth; and including tooth separator means positioned on the front portion of the horizontal wall to be engaged by the user's upper teeth while the clutch is attached to the lower teeth.

7. The clutch of claim 6 wherein said tooth separator means is adapted to be attached to the clutch member in a manner to be readily removed.

8. The clutch of claim 7 wherein said separator has a pair of downwardly extending buttons which mate with snugly fitting apertures on the clutch member so that the separator is easy to install and remove.

9. A dental clutch comprising a thin molded shell having a generally U-shape adapted to fit over the teeth of a human jaw including a horizontal wall extended adjacent the crowns of the teeth, an inner side wall to fit over the inner sides of the teeth and an outer side wall to fit over the outer sides of the teeth, said member being made of a material which is relatively strong but yet can be readily broken, said member having a fracture line in its side walls and horizontal wall which bisects the member into two sections, and means formed on said shell accessible adjacent the patient's mouth for readily breaking the clutch member into two sections along the fracture line by utilizing a suitable tool and thereby facilitating removal of the clutch from the teeth.

10. The clutch of claim 9 including lug means straddling the fracture line in the outer wall of said member sized to form a slot for receiving the flat tip of a screwdriver or similar tool for facilitating breaking the clutch member into two pieces by twisting the tip of the tool in said slot.

11. The clutch member of claim 9 including support means formed integral with the outer side wall and the horizontal wall of said member adapted to extend outwardly through the patient's mouth when the clutch is installed on the teeth, said support means being adapted to receive a horizontally extending rod utilized for mounting other dental apparatus while the clutch is installed on the teeth, said fracture line extending through said support means so that the entire structure can be readily broken into two sections.

12. A dental clutch comprising a member shaped to fit over the teeth of a human jaw and adapted to be attached to the teeth by suitable bonding means, said member including a horizontal wall which extends adjacent the crowns of the teeth and an outer side wall formed integrally with the horizontal wall and extending adjacent the outer sides of the teeth, a support structure formed integral with the clutch member to extend out through the patient's mouth when the clutch member is attached to the teeth, said support structure including a horizontal wall and a pair of spaced vertical walls formed integral with the outer side wall of the clutch member, means defining openings formed in said vertical side walls for receiving a horizontally extending rod for mounting dental apparatus thereon.

13. The clutch of claim 12 wherein the vertical side walls of said support structure are formed of an upper and a lower section which are laterally offset from each other a slight amount along the approximate diameter of said opening, said opening being slightly smaller in diameter than the diameter of the rod to be positioned in the opening so that the structure grips the rod but yet the rod can be readily inserted into the openings by virtue of the offset arrangement of said vertical side walls.

14. The clutch of claim 13 further including a clamp adapted to fit over the support structure and squeeze said upper and lower wall sections to further grip the rod.

15. The clutch of claim 12 including means defining a pair of apertures formed in the horizontal wall of the clutch member and the horizontal wall of the support structure, and separator means having a pair of buttons for being received within said apertures, said separator means having a curved upper surface to be engaged by the upper teeth of the patient while the clutch member is attached to the patient's lower teeth.

16. A dental clutch comprising a member shaped to fit over the teeth of the human jaw including a horizontal wall to fit over the crowns of the teeth and an outer side wall to fit over the outer sides of the teeth, means defining an extension of said horizontal wall adapted to extend outwardly through the patient's mouth when the clutch member is attached to the patient's teeth, tooth separator means attached to said horizontal wall in said extension to be engaged by the patient's upper teeth while the clutch member is attached to the patient's lower teeth so as to space the upper teeth from the clutch member and the lower teeth, said tooth separator having means for permitting the separator to be easily attached to and removed from the clutch member.

17. The tooth separator of claim 16 wherein the tooth separator and the horizontal wall of said member and said extension having mating buttons and holes for removably attaching the separator to the clutch member.

18. The clutch of claim 15 wherein said tooth separator is molded with the clutch member attached to the clutch member by a breakaway section and including one or more additional tooth separators having differing heights molded with said clutch member and attached thereto by breakaway sections, each of said additional tooth separators having means for facilitating their attachment to said horizontal wall and said horizontal extension so that each of the two separators can be easily broken away from the clutch member and the desired separator can be attached to the horizontal wall and extension.

19. A dental clutch comprising a thin-walled shell shaped to fit over the teeth of a human jaw, said shell being sized to permit a quantity of bonding material to fit around the teeth for securing the shell to the teeth, and means formed in said shell to permit the shell to be readily broken into two or more sections so as to facilitate removal of the clutch from the teeth.

20. The clutch of claim 19 including means formed in said shell to facilitate the attachment of said bonding material to said shell.

21. The clutch of claim 19 wherein said member is a molded thin walled shell having a plurality of spaced reinforcing ribs in its side walls.

22. The clutch of claim 19 including support means formed integral with the forward portion of the outer side wall for removably connecting the clutch member to a rod which extends generally horizontally to permit the attachmentn of other dental apparatus such as means for making jaw measurements.

* * * * *

UNITED STATES PATENT OFFICE
CERTIFICATE OF CORRECTION

PATENT NO. : 3,946,489
DATED : March 30, 1976
INVENTOR(S) : Robert L. Lee

It is certified that error appears in the above-identified patent and that said Letters Patent are hereby corrected as shown below:

Column 8, line 24, "tooth separator" should be --clutch--

Column 8, line 29, "15" should be --16--

Signed and Sealed this

Twenty-first Day of September 1976

[SEAL]

Attest:

RUTH C. MASON
*Attesting Officer*

C. MARSHALL DANN
*Commissioner of Patents and Trademarks*